United States Patent [19]

Illum

[11] Patent Number: 4,847,091
[45] Date of Patent: Jul. 11, 1989

[54] PHARMACEUTICAL COMPOSITION INCLUDING SODIUM CROMOGLYCATE

[75] Inventor: Lisbeth Illum, Nottingham, England

[73] Assignee: Fisons plc, Leicestershire, England

[21] Appl. No.: 94,673

[22] PCT Filed: Nov. 28, 1986

[86] PCT No.: PCT/GB86/00726
§ 371 Date: Sep. 23, 1987
§ 102(e) Date: Sep. 23, 1987

[87] PCT Pub. No.: WO87/03197
PCT Pub. Date: Jun. 4, 1987

[30] Foreign Application Priority Data

Nov. 29, 1985 [GB] United Kingdom ............... 8529500
Aug. 30, 1986 [GB] United Kingdom ............... 8621018

[51] Int. Cl.[4] .................................................. A61K 9/66
[52] U.S. Cl. ..................................... 424/455; 424/45; 424/46; 424/426

[58] Field of Search ............... 424/422, 423, 427, 428, 424/455, 451, 400, 45, 46, 426

[56] References Cited

U.S. PATENT DOCUMENTS 3,425,962 2/1969 Granatek et al. ................. 424/79 X
4,057,556 11/1977 Bagli .............................. 514/534 X
4,221,778 9/1980 Raghunathan ................... 424/79 X

FOREIGN PATENT DOCUMENTS 0023359 7/1979 European Pat. Off. .
0171528 2/1986 European Pat. Off. .

Primary Examiner—Thurman K. Page
Attorney, Agent, or Firm—Marshall, O'Toole, Gerstein, Murray & Bicknell

[57] ABSTRACT

Pharmaceutical compositions comprising microspheres incorporating sodium cromoglycate, wherein the microspheres comprise material having ion-exchange properties.

10 Claims, No Drawings

PHARMACEUTICAL COMPOSITION INCLUDING SODIUM CROMOGLYCATE

This invention relates to pharmaceutical compositions.

Sodium cromoglycate has been known for a number of years for the treatment of allergic conditions, for example asthma, hay fever, vernal keratoconjunctivitis and rhinitis; however it suffers from the disadvantage that it is of relatively short duration of action.

Microspheres have been proposed as drug delivery systems for numerous therapeutic areas including oral delivery of tetracycline, oral and intramuscular delivery of insulin for treatment of diabetes, subcutaneous delivery of local anaesthetics, delivery of cytostatics to various organs and intra-arterial coadministration with cytostatics, and as local dosage forms for e.g. ophthalmic, intra-articular, intramuscular, percutaneous, subcutaneous and nasal use.

Known microsphere formulations of sodium cromoglycate, however, suffer from the disadvantage that release of drug from the microspheres is very rapid, leading to a short duration of action and a requirement for frequent application.

We have now found a pharmaceutical microsphere formulation of sodium cromoglycate which substantially overcomes or mitigates these disadvantages.

Thus, according to the invention there is provided a pharmaceutical composition comprising microspheres incorporating sodium cromoglycate, wherein the microspheres include material having ion-exchange properties.

The microspheres are preferably formed from biodegradable material. The material should be compatible with sodium cromoglycate. Suitable biodegradable materials which have ion-exchange properties include suitable modified polymeric carbohydrates, e.g. diethylaminoethyl dextran. Alternatively the microspheres may comprise, as a first component, a biodegradable polymeric material not having ion-exchange properties and, as a second component, a biodegradable polymeric material having ion-exchange properties. The weight ratio of first component to second component is preferably from about 1:1 to 50:1, more preferably from about 1:1 to 25:1. Suitable biodegradable materials not having ion-exchange properties include carbohydrates e.g. starch and dextran; modified carbohydrates such as dextran cross-linked with epichlorhydrin e.g. the material known as dextranomer; serum albumin, e.g. rabbit, bovine or human serum albumin; gelatin; polyacrylamide and polycyanoacrylate; polyacryldextran and polyalkylcyanoacrylate. Polymeric materials which have ion-exchange properties include suitable modified carbohydrates e.g. diethylaminoethyl dextran.

The microspheres according to the invention may be prepared by procedures known in the art. In general microspheres including sodium cromoglycate may be prepared either by emulsifying aqueous solutions of microsphere material, e.g. diethylaminoethyl dextran, and sodium cromoglycate in a non-aqueous medium, e.g. olive oil or cotton seed oil, or by soaking preformed microspheres in a solution of sodium cromoglycate. In the former method of preparation of microspheres, a cross-linking agent may also be included in the aqueous solution. In either case, the microspheres may be removed by filtration, washed, e.g. with ether, and freeze dried.

The preferred size of the microspheres depends on the material used for the microsphere, the target organ(s), the disease being treated and the mode of administration.

In general, we prefer microspheres with a mean diameter between 1 $\mu$m and 200 $\mu$m. Microspheres for administration to the lung, e.g. as an entrained aerosol powder or as a pressurised aerosol, preferably have a mean diameter from 1 to 10 $\mu$m, more preferably 3 to 8 $\mu$m. For administration to the nose as an insufflated powder, the microspheres preferably have a mean diameter of from 5 to 200 $\mu$m, more preferably 75 to 100 $\mu$m. Microspheres for administration to the nose as a pressurised aerosol preferably have a mean diameter of from 1 to 10 $\mu$m, more preferably 3 to 8 $\mu$m. Microspheres may also be applied to the eye, e.g. as a suspension, and preferably have a mean diameter less than 30 $\mu$m, e.g. 10 to 25 $\mu$m. Microspheres incorporating sodium cromoglycate may also be applied to leg ulcers, ischaemic ulcers, open wounds, etc.

The mean diameter of the microspheres may be selected by fractionation or by varying one of the manufacturing parameters. In general the mean diameter is inversely proportional to the viscosity of the non-aqueous medium. Thus lowering the viscosity of olive oil by the addition of petroleum ether leads to an increase in the mean diameter of the microspheres. Higher stirring speeds lead to smaller microspheres. The mean diameter of large microspheres may be reduced by sonication.

The degree of incorporation of sodium cromoglycate in the microspheres will depend inter alia upon the method of preparation of the microspheres and on the characteristics of the material used in the microsphere. We prefer the weight ratio of sodium cromoglycate to ion-exchange material to be between 0.1:1 and 4:1, more preferably between 0.5:1 and 2:1.

The rate of release of sodium cromoglycate from the microspheres depends, amongst other factors, on the type of microsphere, degree of denaturation, degree of cross-linking and/or presence of additional ionic agents, e.g. cationic agents.

Suitable cross-linking agents include glutaraldehyde. Additional ionic agents, e.g. ammonium salts, may be incorporated into the microspheres after cross-linking, e.g. by quenching glutaraldehyde with appropriate amines, or by incorporating an amine modified material such as diethylaminoethyl dextran in the microsphere.

The microspheres of the present invention are advantageous in that they are more efficacious, have a longer duration of action, improve the bioavailability of the drug, can be used at lower doses, require less frequent adminstration or produce less side-effects than known formulations of sodium cromoglycate.

The longer duration of action may arise as a result of improved drug release characteristics or of slower clearance of the microspheres from the site of application, for instance delayed mucociliary clearance when applied to the nose, or to both of these factors. The slower rate of clearance may be due to improved bioadhesive properties of the microspheres.

The microspheres of the present invention have the further advantage that they retain the sodium cromoglycate when suspended in water; they may thus be presented to the patient as an aqueous suspension.

Thus, according to another aspect of the invention, we provide an aqueous suspension of microspheres including sodium cromoglycate, wherein the microspheres comprise material having ion-exchange properties.

Conditions of the outer eye in which the composition of the invention may be used include vernal catarrh (vernal kerato-conjunctivitis) and marginal corneal ulceration or infiltration. Other conditions which may be treated using the composition of the invention include the occular effects of hay fever, 'allergic eyes' where the allergen is known or unknown and spring/summer conjunctivitis. This latter term is used to mean allergic disorders of the eyes occurring in the spring and summer where an external allergen plays a part in the disorder. Further conditions of the eye which may be mentioned are 'irritable eye' or 'non-specific conjunctivitis', dry eye syndrome, Herpes Zoster Keratitis and Conjunctivitis, adenovirus infections, phlyctenular conjunctivitis, corneal homograft rejection, Trachoma, anterior uveitis, anterior eye chamber disorders and drug sensitivity.

Conditions of the nose which may be mentioned include seasonal rhinitis, e.g. hay fever; perennial rhinitis, nasal polyps and allergic manifestations of the nasopharynx.

Conditions which may be treated by administration of the microspheres of the present invention to the lung include so-called "extrinsic" allergic asthma, "intrinsic" asthma (in which no sensitivity to extrinsic antigen can be demonstrated), hay fever, urticaria and auto-immune diseases.

According to a further aspect of the invention, there is provided a method of treating an allergic condition, which comprises administering an effective amount of the composition of the invention to a patient suffering from such a condition.

The invention will now be illustrated, but in no way limited, by the following Examples.

EXAMPLE 1

Diethylaminoethyl dextran: 55.6% w/w
Sodium cromoglycate: 44.4% w/w

Pre-formed diethylaminoethyl dextran microspheres were allowed to swell in water overnight. A concentrated (4% w/v) solution of sodium cromoglycate was then added to the swollen microspheres and stirred for 15 minutes, after which the particles were collected on a micromesh filter (pore size 5 μm) and freeze-dried.

EXAMPLE 2

Rabbit serum albumin: 89.3% w/w
Sodium cromoglycate: 7.1% w/w
Diethylaminoethyl dextran: 3.6% w/w Highly purified olive oil (50 ml) was mixed with petroleum ether (75 ml) and prestirred for 5-10 minutes in a 250 ml beaker using a Heidolph mixer fitted with a four bladed axial-flow impeller. 0.4 ml of an aqueous solution containing 25% w/v rabbit serum albumin, 2% w/v sodium cromoglycate and 1% w/v diethylaminoethyl dextran in phosphate buffer (pH=7.4) was added dropwise to the mixture and stirring was continued at 700 revolutions per minute for 15 minutes.

The albumin microspheres were stabilized by the dropwise addition of 0.1 ml of a 25% 1,5-glutaraldehyde solution under continuous stirring for 15 minutes. The microsphere emulsion was then centrifuged, the spheres resuspended in petroleum ether and filtered through a micromesh filter (pore size 5 μm). Finally they were washed with petroleum ether and ethanol and freeze-dried overnight.

EXAMPLE 3

Rabbit serum albumin: 86.2% w/w
Sodium cromoglycate: 6.9% w/w
Diethylaminoethyl dextran: 6.9% w/w Prepared by the method of Example 2 using an aqueous solution containing 25% w/v rabbit serum albumin, 2% w/v sodium cromoglycate and 2% w/v diethylaminoethyl dextran.

EXAMPLE 4

Rabbit serum albumin: 80.6% w/w
Sodium cromoglycate: 6.5% w/w
Diethylaminoethyl dextran: 12.9% w/w Prepared by the method of Example 2 using an aqueous solution containing 25% w/v rabbit serum albumin, 2% w/v sodium cromoglycate and 4% w/v diethylaminoethyl dextran.

I claim:

1. A pharmaceutical composition comprising microspheres incorporating sodium cromoglycate, wherein the microspheres include biodegradable polymeric material having ion-exchange properties.

2. A pharmaceutical composition according to claim 1 wherein the ion-exchange material is a modified carbohydrate.

3. A pharmaceutical composition according to claim 1 wherein the ion-exchange material is diethylaminoethyl dextran.

4. A pharmaceutical composition according to claim 1 wherein the microspheres have a mean diameter of between 1 and 200 μm.

5. A pharmaceutical composition according to claim 1 wherein the microspheres have a mean diameter of between 75 and 100 μm.

6. A pharmaceutical composition according to claim 1 wherein the microspheres have a mean diameter of between 1 and 10 μm.

7. A pharmaceutical composition according to claim 1 wherein the weight ratio of sodium cromoglycate to ion-exchange material is between 0.1:1 and 4:1.

8. A pharmaceutical composition according to claim 1 wherein the weight ratio of sodium cromoglycate to ion-exchange material is between 0.5:1 and 2:1.

9. A pharmaceutical composition according to claim 1 which is an aqueous suspension.

10. A method of treatment of an allergic condition, comprising administration of a therapeutically effective amount of a pharmaceutical composition according to claim 1 a patient suffering from such a condition.

* * * * *